(12) United States Patent
Zhang et al.

(10) Patent No.: US 7,718,969 B2
(45) Date of Patent: May 18, 2010

(54) METHODS AND SYSTEMS FOR GENERATING AMPLIFIED TERAHERTZ RADIATION FOR ANALYZING REMOTELY-LOCATED OBJECTS

(75) Inventors: Xi-Cheng Zhang, Melrose, NY (US); Jianming Dai, Troy, NY (US); Xu Xie, Troy, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 333 days.

(21) Appl. No.: 11/756,243

(22) Filed: May 31, 2007

(65) Prior Publication Data

US 2008/0048122 A1    Feb. 28, 2008

Related U.S. Application Data

(63) Continuation of application No. 11/610,824, filed on Dec. 14, 2006.

(60) Provisional application No. 60/868,148, filed on Dec. 1, 2006, provisional application No. 60/754,096, filed on Dec. 27, 2005.

(51) Int. Cl.
   *G01N 21/35* (2006.01)

(52) U.S. Cl. .................................. 250/341.8

(58) Field of Classification Search ............... 250/341.1
   See application file for complete search history.

(56) References Cited

U.S. PATENT DOCUMENTS 5,939,721 A    8/1999   Jacobsen et al.  ............ 250/330

| 6,111,416 A | 8/2000 | Zhang et al. | 324/753 |
| 6,977,379 B2 | 12/2005 | Zhang et al. | 250/341.1 |
| 2005/0242287 A1 | 11/2005 | Hakimi | 250/363.09 |
| 2005/0282407 A1 | 12/2005 | Bruland et al. | 438/795 |

FOREIGN PATENT DOCUMENTS

| GB | 2396695 | 6/2004 |
| GB | 2399626 | 9/2004 |
| WO | WO 00/75641 | 12/2000 |

OTHER PUBLICATIONS

A. Couairon et al., "Propagation of twin laser pulses in air and concatenation of plasma strings produced by femtosecond infrared filaments." Optics Communications 225 (2003) 177-192. DOI: 10.1016/j.optcom.2003.07.011.*

(Continued)

*Primary Examiner*—Constantine Hannaher
(74) *Attorney, Agent, or Firm*—Heslin Rothenberg Farley & Mesiti P.C.

(57) ABSTRACT

A method for generating amplified terahertz radiation includes inducing a first volume of a gas to produce a seed plasma and emit pulsed seed terahertz radiation by focusing an optical seed beam in the first volume. The seed terahertz radiation is then amplified by focusing an optical gain beam to produce a gain plasma in a second volume overlapping with the pulsed seed terahertz radiation remote from the seed plasma. The method may be implemented in a system for detecting and analyzing a remotely-located object such as an explosive material, a biological agent, and a chemical agent.

43 Claims, 11 Drawing Sheets

OTHER PUBLICATIONS

T.R. Nelson et al., "Laser filamentation of a femtosecond pulse in air at 400nm." QELS '01 Technical Digest, Summaries of Papers Presented at the Quantum Electronics and Laser Science Conference, 2001 (2001) 261-262. DOI: 10.1109/QELS.2001.962222.*

Zandonella, Catherine, "T-Ray Specs," Nature, vol. 424, pp. 721-722, Aug. 14, 2003.

Bartel et al., "Generation of Single-Cycle THZ Transients with High Electric-Field Amplitudes," Optics Letters, vol. 30, No. 20, pp. 2805-2807, Oct. 15, 2005.

Cook et al., "Intense Terahertz Pulses by Four-Wave Rectification in Air," Optics Letters, vol. 25, No. 16, pp. 1210-1212, Aug. 15, 2000.

Dai et al., "Detection of Broadband Terahertz Waves with a Laser-Induced Plasma in Gases," Physical Review Letters, vol. 97, pp. 103903-1 to 103903.4, Sep. 8, 2006.

Ferguson et al., "Materials for Terahertz Science and Technology," Nature Materials, vol. 1, pp. 26-33, Sep. 2002.

Hamster et al., "Short-Pulse Terahertz Radiation from high-Intensity-Laser-Produced Plasmas," Physical Review, vol. 49, No. 1, pp. 671-677, Jan. 1994.

Janke et al., "Inversionless Amplification of Coherent Terahertz Radiation," Physical Review Letters, vol. 67, pp. 155206-1 to 155206-4, Apr. 28, 2003.

Kress et al., "Determination of the Carrier-Envelope Phase of Few-Cycle Laser Pulses with Terahertz-Emission Spectroscopy," Nature Physics, vol. 2, pp. 327-331, May 2006.

Kress et al., "Terahertz-Pulse Generation by Photoionization of Air with Laser Pulses Composed of Both Fundamental and Second-Harmonic Waves," Optics Letters, vol. 29, No. 10, pp. 1120-1122, May 15, 2004.

Löffler et al., "Efficient Terahertz Pulse Generation in Laser-Induced Gas Plasmas," Acta Physica Polonica A, vol. 107, No. 1, pp. 99-108, 2005.

Martini et al., "Inversionless Amplification of Coherent THz Radiation," IEEE, pp. 242-245, 1998. THz 98, IEEE 6th Intl Conf on THz Electronics, Sep. 3-4, 1998.

Meyer et al., "Phase-Matched High-Order Difference-Frequency Mixing in Plasmas," Physical Review Letters, vol. 26, No. 18, pp. 3336-3339, Apr. 29, 1996.

Théberge et al., "Tunable Ultrashort Laser Pulses Generated Through Filamentation in Gases," Physical Review Letters, vol. 97, pp. 023904-1 to 023904-5, Jul. 14, 2006.

Tzortzakis et al., "Coherent Subterahertz Radiation from Femtosecond Infrared Filaments in Air," Optics Letters, vol. 27, No. 21, pp. 1944-1946, Nov. 1, 2002.

Van Exter et al., "High-Brightness Terahertz Beams Characterized with an Ultrafast Detector," Applied Physics Letters, vol. 55, No. 4, pp. 337-339, Jul. 24, 1989.

Wu et al., "Broadband Detection Capability of ZnTe Electro-Optic Field Detectors," Applied Physics Letters, vol. 68, No. 21, pp. 2924-2926, May 20, 1996.

Xie et al, "Coherent Control of THz Wave Generation in Ambient Air," Physical Review Letters, vol. 96, pp. 075005-1 to 075005-4, Feb. 24, 2006.

Xie et al., "Enhancement of Terahertz Wave Generation from Laser Induced Plasma," Applied Physics Letters, vol. 90, 2007, 141104, 3-pages, Apr. 4, 2007.

Zhang et al., pending U.S. Appl. No. 11/610,824 filed Dec. 14, 2006 entitled "Method of Analyzing A Remotely-Located Object Utilizing an Optical Technique to Detect Terahertz Radiation".

Zhang et al., pending U.S. Appl. No. 11/756,230 filed May 31, 2007, entitled "Methods and Systems for the Enhancement of Terahertz Wave Generation for Analyzing A Remotely-Located Object".

Zhu et al., "Long Lifetime Plasma Channel in Air Generated by Multiple Femtosecond Laser Pulses and an External Electrical Field," Optics Express, vol. 14, No. 11, pp. 4915-4922, May 29, 2006.

Agrawal, Govind P., "Nonlinear Fiber Optics," Third Edition, Academic Press, San Diego, 1-page, 2001, cover only.

Reimann, et al., "Direct Field-Resolved Detection of Terahertz Transients with Amplitudes of Megavolts per Centimeter," Optics Letters, vol. 28, No. 6, pp. 471-473, Mar. 15, 2003.

Zhang et al., International Search Report, PCT Patent Application No. PCT/US2006/062091 (5 pages), entitled "Method of Analyzing A Remotely Located Object Utilizing an Optical Technique to Detect Terahertz Radiation," filed Dec. 14, 2006 (5 pages), not a publication.

Federicli, John F. et al., "THz Standoff Detection and Imaging of Explosives and Weapons," Optics and Photonics in Global Homeland Security, Proc. SPIE, vol. 5781, pp. 75-84 (2005).

G. Méchain, A. Mysyrowicz, M. Depiesse, M. Pellett, "A Virtual Antenna Produced In Air By Intense Femtosecond Laser Pulses," (Nov. 3, 2005), Proc. SPIE, vol. 5989, 59890S (2005) DOI; 10.1117/12.631202 (6 Pages).

Carr et al., "High-Power Terahertz Radiation From Relativistic Electrons," Nature, vol. 420, pp. 153-156, Nov. 2002.

Chin et al., "The Propagation of Powerful Femtosecond Laser Pulses in Optical Media: Physics, Application, and New Challenges [1,2]," Canadian Journal of Physics, vol. 83, No. 9, pp. 863-905, Sep. 2005.

Cole et al., "Coherent Manipulation of Semiconductor Quantum Bits with Terahertz Radiation," Nature, vol. 410, pp. 60-63, Mar. 2001.

Cook et al., "Terahertz-Field-Induced Second-Harmonic Generation Measurements of Liquid Dynamics," Chemical Physics Letters, vol. 309, pp. 221-228, Aug. 13, 1999.

Grischkowsky et al., Far-infrared Time-Domain Spectroscopy with Terahertz Beams of Dielectrics and Semiconductors, J. Optical Society America B, vol. 7, No. 10, pp. 2006-2015, Oct. 1990.

Huber et al., "How Many-Particle Interactions Develop After Ultra Fast Excitation of an Electron-Hole Plasma," Nature, vol. 414, pp. 286-289, Nov. 2001.

Kaindl et al., "Ultrafast terahertz Probes of Transient Conducting and Insulation Phases in an Electron-Hole Gas," Nature, vol. 423, pp. 734-738, Jun. 12, 2003.

Köhler et al., "Terahertz Semiconductor-Heterostructure Laser," Nature, vol. 417, pp. 156-159, May 9, 2002.

Nahata et al., "Detection of Freely Propagating Terahertz Radiation by Use of Optical Second-Harmonic Generation," Optics Letters, vol. 23, No. 1, pp. 67-69, Jan. 1, 1998.

Wang et al., "Metal Wires for Terahertz Wave Guiding," Nature, vol. 432, pp. 376-379, Nov. 18, 2004.

Wu et al., "Free-Space Electro-Optic Sampling of Terahertz Beams," American Physics Letters, vol. 67, No. 24, pp. 32523-3525, Dec. 11, 1995.

Zhong et al., "Terahertz Emission Profile From Laser-Induced Air Plasma," Applied Physics Letters, vol. 88, pp. 261103-1-261103-3, 2006.

Hamster et al., "Subpicosecond, Electromagnetic Pulses from Intense Laser-Plasma Interaction," Physical Review Letters, vol. 71, No. 17, pp. 2725-2728, Oct. 25, 1993.

Walsh et al., "The Tunnel Ionization of Atoms, Diatomic and Triatomic Molecules Using Intense 10.6 μm Radiation," Phys. B: At. Mol. Opt. Phys. vol. 27, pp. 3767-3779, 1994.

* cited by examiner

METHODS AND SYSTEMS FOR GENERATING AMPLIFIED TERAHERTZ RADIATION FOR ANALYZING REMOTELY-LOCATED OBJECTS

CLAIM TO PRIORITY AND CROSS-REFERENCE TO RELATED APPLICATIONS

This application claims priority under 35 U.S.C. §119 to U.S. Provisional Application No. 60/868,148, filed Dec. 1, 2006, entitled "Observation of Terahertz Wave Amplification in Laser-Induced Air Plasma", which is herein incorporated by reference in its entirety.

This application is also a continuation-in-part application of commonly owned pending U.S. patent application Ser. No. 11/610,824 filed Dec. 14, 2006, entitled "Method of Analyzing A Remotely-Located Object Utilizing An Optical Technique To Detect Terahertz Radiation" which claims priority under 35 U.S.C. §119 to U.S. Provisional Application No. 60/754,096, filed Dec. 27, 2005, the entire subject matter of these applications are incorporated herein by reference.

This application is related to commonly owned and concurrently filed U.S. patent application Ser. No. 11/756,230, entitled "Methods And Systems For The Enhancement Of Terahertz Wave Generation For Analyzing A Remotely-Located Object", which claims priority under 35 U.S.C. §119 to U.S. Provisional Application No. 60/868,140, filed Dec. 1, 2006, entitled "Enhancement of THz Wave Generation From Laser Induced Plasma", the entire subject matter of these applications are incorporated herein by reference.

GOVERNMENT RIGHTS STATEMENT

This invention was made with U.S. Government support under Grant No. ECS-0621522 from the National Science Foundation and Grant No. DAAD 19-02-1-0255 from the Army Research Office. The U.S. Government has certain rights in the invention.

FIELD OF THE INVENTION

The present invention generally relates to generating and detecting terahertz radiation. More particularly, the present invention relates to utilizing optical-wavelength radiation to facilitate remote analysis of an object with terahertz radiation.

BACKGROUND OF THE INVENTION

Improvised explosive devices (IEDs) are extremely dangerous partially because they are difficult to identify. A device capable of remote and in situ monitoring to detect concealed explosives would be very beneficial for a number of defense and homeland security uses.

Since terahertz wave spectroscopy has been utilized to detect a number of chemical and explosive materials and related compounds by providing their spectral signatures in the terahertz frequency range, it may have use in defense and security applications. For example, there is interest in terahertz wave spectroscopy as a technique to sense improvised explosive devices (IEDs). However, due to severe water vapor attenuation of terahertz waves in the atmosphere, reliable sensing range of terahertz wave spectroscopy has been limited to relatively short distances. For example, even though propagation of a pulsed terahertz wave for more than 145 meters has been achieved, spectroscopic measurement with an acceptable signal-to-noise ratio and false alarm rate is limited to about 30 meters. For defense and security applications, it is desirable to increase the reliable sensing range of terahertz wave spectroscopy.

There is a need for further techniques for increasing the generation of terahertz waves, for increasing the range at which terahertz waves may be reliably sensed under a range of atmospheric conditions, and for decreasing the sensitivity to the humidity level.

SUMMARY OF THE INVENTION

The present invention provides, in a first aspect, a method for generating terahertz radiation. The method includes inducing a first volume of a gas to produce a seed plasma and emit pulsed seed terahertz radiation by focusing an optical seed beam in the first volume, and amplifying the seed terahertz radiation by focusing an optical gain beam to produce a gain plasma in a second volume overlapping with the pulsed seed terahertz radiation remote from the seed plasma.

The present invention provides, in a second aspect, a system for generating terahertz seed radiation. The system includes a source for an optical seed beam, means for focusing the optical seed beam to produce a focused optical seed beam that ionizes a first volume of a gas to produce a seed plasma to emit pulsed seed terahertz radiation, a source for an optical gain beam, and means for focusing the optical gain beam to produce a focused optical gain beam in a second volume to produce a gain plasma to amplify the pulsed terahertz radiation, the second volume overlapping with the pulsed seed terahertz radiation remote from the seed plasma.

The present invention provides, in a third aspect, a method for detecting a remotely-located object. The method includes inducing a first volume of a gas to produce a seed plasma to emit pulsed seed terahertz radiation directed toward a targeted object by focusing an optical seed beam in the volume, amplifying seed terahertz radiation directed toward the target by focusing an optical gain beam to produce a gain plasma in a second volume overlapping with the pulsed seed terahertz radiation remote from the seed plasma, ionizing a third volume of the ambient gas to produce a sensor plasma by focusing an optical probe beam in the third volume, and detecting an optical component of resultant radiation produced from an interaction of the focused optical probe beam and an incident terahertz radiation in the sensor plasma, the incident terahertz radiation being produced by an interaction of the amplified pulsed seed terahertz radiation with the targeted object.

The present invention provides, in a fourth aspect, a system for detecting a remotely-located object. The system includes a source for an optical seed beam, means for focusing the optical seed beam to produce a focused optical seed beam in a first volume of a gas to produce a seed plasma and induce an emission, from the seed plasma, of pulsed seed terahertz radiation directed toward a targeted object, a source for an optical gain beam, means for focusing the optical gain beam to produce a focused optical gain beam in a second volume of the ambient gas overlapping with the seed terahertz radiation remote from the seed plasma to amplify seed terahertz radiation directed toward the targeted object, a source for an optical probe beam, means for focusing the optical probe beam to produce a focused optical probe beam that ionizes a third volume of the ambient gas to produce a sensor plasma, and an optical detector for detecting an optical component of resultant radiation produced from an interaction of a focused optical probe beam and an incident terahertz radiation in the sensor plasma, the incident terahertz radiation being produced by an interaction of amplified seed terahertz radiation with the targeted object.

BRIEF DESCRIPTION OF THE DRAWINGS

The present matter which is regarded as the invention is particularly pointed out and distinctly claimed in the concluding portion of the specification. The present invention, however, may best be understood by reference to the following detailed description of various embodiments and the accompanying drawings in which:

DETAILED DESCRIPTION OF THE INVENTION

Figure 1:
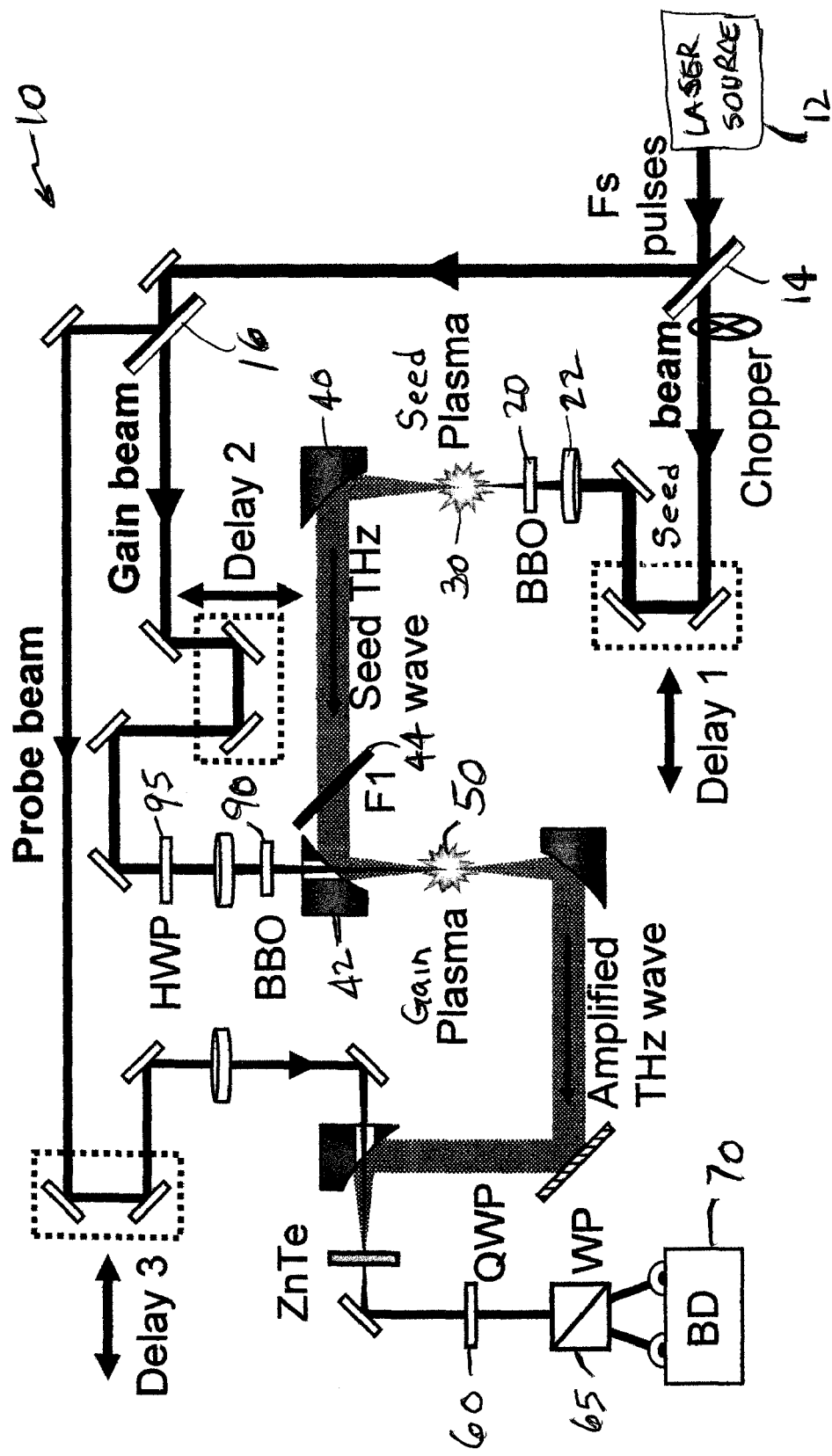
FIG. 1 is the schematic illustration of an experimental setup in accordance with the present invention for generating amplified terahertz radiation in which an optical beam from a laser source is split into three beams, for example, an optical seed beam, an optical gain beam, and an optical probe beam.

Pulsed terahertz wave spectroscopy is capable of sensing at short ranges compounds from which improvised explosive devices (IEDs) may be made. For example, the compound RDX has been detected at distances up to 30 meters in good weather, but the detection range using terahertz radiation may decrease to less than 10 meters in humid conditions. The reason is that the propagation of a terahertz wave in air is largely limited by water vapor absorption. For example, the attenuation of terahertz waves through the atmosphere is greater than 100 dB/km, even when the humidity level is only 20% at room temperature. Measurements of the attenuation effect at humidity levels from 3% to 100% indicate that, in ambient air, it may not be practical to get useful terahertz spectroscopy information from a terahertz wave traveling more than 100 meters. On the other hand, optical pulses (i.e. pulses of visible light, for example) have a significantly lower attenuation (on the order of 0.01 dB/km) than terahertz waves in the air.

Because optical pulses may be used to generate terahertz waves and to sense the incident terahertz waves, optical radiation may be used advantageously in terahertz spectroscopy for remote generation and detection of terahertz waves to solve the problem of high attenuation of terahertz radiation in the atmosphere and thereby increase the effective range at which terahertz spectroscopy can detect explosive materials.

In one aspect, the present invention provides a technique for amplification of terahertz (THz) wave in laser-induced plasma in gases. For example, when a seed THz wave is sent into the 5 mm long plasma created by focusing a 120 femtosecond pulse duration and 800 nm center wavelength beam and its second-harmonic into an ambient gas such as air, a maximum gain of 4.5/cm at the 0.5 THz component with an entire gain bandwidth over 1 THz is measured with total optical excitation intensity of $8 \times 10^{14}$ W/cm$^2$. The amplification effect occurs within a time scale of less than 400 femtoseconds of the onset of ionization processes due to the optical excitation pulse duration.

In another aspect, the present invention provides a technique that utilizes the amplified terahertz radiation to detect a remotely-located object such as explosives and explosive related compounds from a distance. As described in greater detail below, a plurality of temporally separated pulsed optical beams may be focused to ionize a volume of ambient gas close to the targeted object and generate an amplified terahertz wave emitter plasma (i.e., a gain plasma). Another optical beam may be focused to ionize a volume of ambient gas to produce a terahertz wave sensor plasma. The sensor plasma may detect an incident terahertz wave that results from the amplified terahertz radiation's interaction with the target. Interaction of the amplified terahertz radiation with the target includes reflection, scattering, and transmission of the amplified terahertz radiation by the target. An explosive or related compound may be detected by identifying the specified spectral fingerprint of the material in the terahertz wave detected by the sensor plasma.

Initially, with reference to FIG. 1, therein illustrated is an experimental setup 10 which demonstrates the amplification of the terahertz wave in accordance with the present invention.

Laser pulses from a laser source 12 such as a Ti:sapphire amplifier, delivering 800 μJ, 120 fs pulses at a repetition rate of 1 kHz with a central wavelength at 800 nm), are split into three parts. A first optical beam produces a first plasma 30 to generate terahertz waves, a second optical beam produces a gain plasma 50 to amplify the terahertz waves, and a third optical beam is used to detect the amplified terahertz waves. For example, the laser pulses are split by a beamsplitter 14 into a first optical beam or an optical seed beam, and a second optical beam which second optical beam is further split by a beamsplitter 16 into an optical gain beam and an optical probe beam.

The optical seed beam and its second harmonic, after passing through a nonlinear optical crystal 20 such as a 100 μm thick type-1 beta barium borate (BBO) crystal, is focused using a lens 22 into an ambient gas such as air to produce seed plasma 30, generating a highly directional broadband terahertz wave. The generated terahertz wave, which serves as the input terahertz signal or seed terahertz wave, is then collimated and focused through two parabolic mirrors 40 and 42 at the same spot as the gain beam is focused at. The seed terahertz wave may be filtered with a filter 44 such as a high-resistivity silicon filter.

To amplify the seed terahertz wave, the seed terahertz wave and the optical gain beam are focused at the same point in a collinear or a quasi-collinear configuration. The optical gain beam produces gain plasma 50 in the seed terahertz wave. The outputted amplified terahertz wave may be finally measured using the optical probe beam with a ZnTe crystal via electro-optic sampling employing a quarter waveplate 60; Wollaston prism 65, and a balanced detector 70. The optical pump beam, the optical gain beam, and the optical probe beam may be delayed by three translation stages (e.g., delays) to individually control the timing between the seed terahertz wave, the optical gain pulse, and the optical probe pulse.

First, the terahertz amplification effect in the gain plasma generated by the optical gain beam with only the fundamental (ω, 800 nm) wavelength was studied, i.e., without the second BBO crystal in the optical gain beam.

Figure 2A:
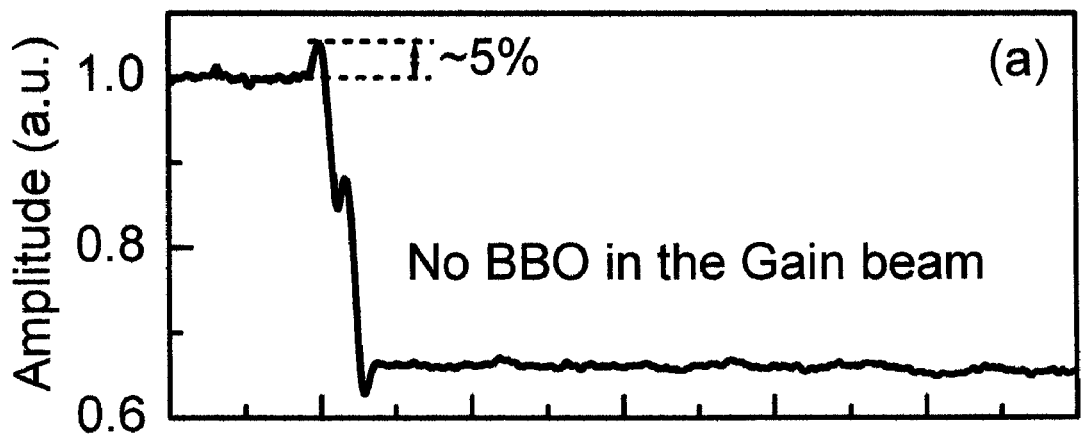
FIGS. 2A and 2B are plots of a typical pump-probe decay obtained by scanning an optical gain beam delay 2 using the experimental setup of FIG. 1 while keeping an optical pump beam delay 1 and an optical probe beam delay 3 fixed at a peak of a seed (or amplified) THz waveform, without a BBO crystal in the optical gain beam, and with a BBO crystal in the optical gain beam.

FIG. 2A plots the terahertz wave field amplitude in a pump-probe scheme obtained by scanning the optical gain beam (Delay 2) while fixing the relative time delay between the optical pump beam (Delay 1) and the optical probe beam (Delay 3) at the peak terahertz signal. As shown in FIG. 2A, around the zero-delay, there is an increase of about 5% in the input peak terahertz signal (peak of seed terahertz wave) after passing through the air plasma generated by the 800 nm optical gain beam with an intensity of $8 \times 10^{14}$ W/cm$^2$. After the zero-delay, the peak terahertz signal is decreased because of the plasma screening effect to the terahertz waves. Further experimental results show that the enhancement around the zero-delay (with all the delays set at zero) is very sensitive to the polarization of the optical gain beam. This result may exclude the plasma lensing effect, in which the terahertz beam profile is modified by the plasma and the final detection efficiency is increased or decreased.

Figure 2B:
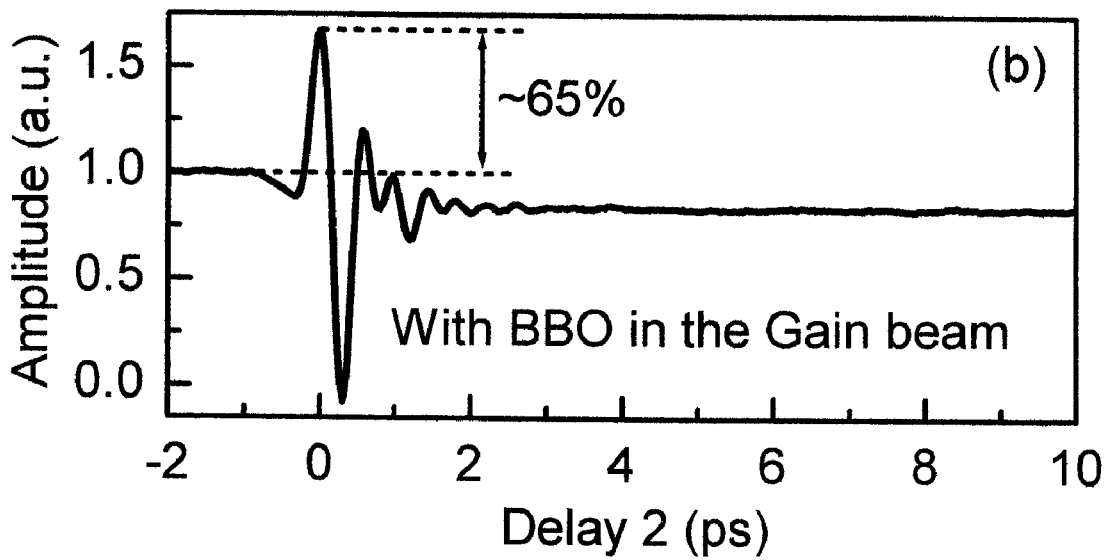

With reference again to FIG. 1, the same experimental procedure as above was repeated with a BBO crystal 90 inserted in the optical gain beam to generate a second-harmonic (400 nm), which is mixed with the residual 800 nm optical beam in the gain plasma. FIG. 2B plots the optical pump-probe decay. It is noted that the "zero-delay" for optical gain beam is reset due to the insertion of BBO crystal 90. By properly adjusting the rotation angle of both BBO crystal 90 and a half-wave plate 95 in the optical gain beam, an increase of about 65% in peak input terahertz signal is observed with a total optical gain beam intensity of about $8 \times 10^{14}$ W/cm$^2$. As explained above, without the second harmonic (BBO crystal 90 removed) in the optical gain beam, only a 5% increase of the seed terahertz signal was achieved. The same terahertz wave amplitude reduction is observed for a longer time after the conductive plasma is completely formed.

Figure 3:
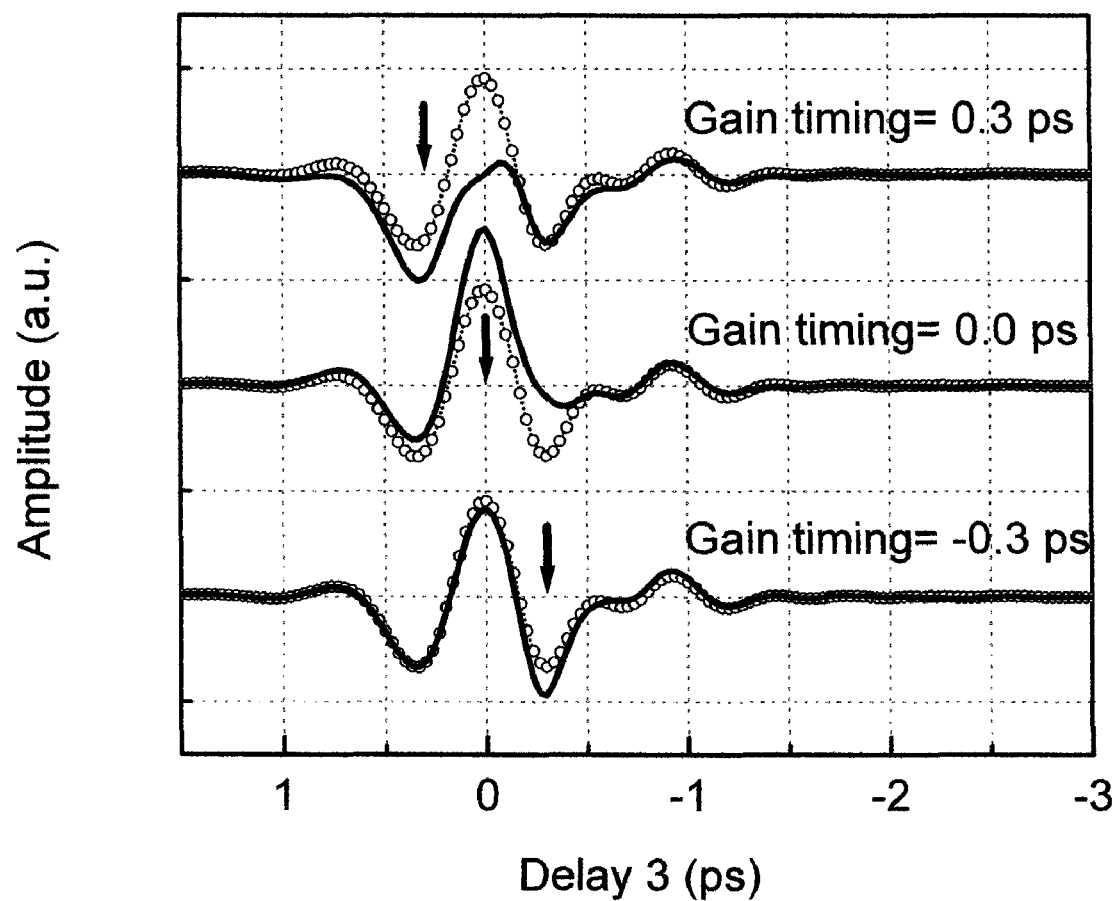
FIG. 3 is a plot of terahertz waveforms (solid lines) obtained using the experimental setup of FIG. 1 by scanning optical probe beam Delay 3 with different optical gain beam Delay 2 set at 0.3 ps, 0.0 ps, and −0.3 ps while fixing an optical pump beam Delay 1 at zero timing, and with a plot of identical seed terahertz waveforms (circles) obtained by blocking the optical gain beam illustrated for comparison.

FIG. 3 are plots of three terahertz waveforms obtained by scanning optical probe beam Delay 3 with three different optical gain beam delay 2, one set at 0.3 ps, one set at 0.0 ps, and one set at −0.3 ps, while fixing optical pump beam Delay 1 at zero timing. Three identical seed terahertz waveforms (circles) obtained by blocking the optical gain beam are displayed in each of the three cases for comparison. All the waveforms are deformed because the amplification is only obtained in a time window of about 400 fs, as shown in FIG. 2A and 2B. Vertical arrows indicate the corresponding gain pulse positions.

Three physical mechanisms might possibly contribute to the observed enhancement of the seed terahertz wave. First, there is constructive/destructive interference between the seed terahertz wave and the terahertz wave generated by the optical gain beam. Second, the seed terahertz beam profile (spatial, temporal, and divergence angle) is modified by the conductive plasma induced by the optical gain beam. Third, the nonlinear optical parametric processes participate in the amplification.

In order to locate the dominant mechanism in the terahertz wave enhancement/amplification in the laser-induced plasma, additional experiments were performed. In a first experiment, the amplified terahertz signal using a seed terahertz signal at different amplitudes or with a flipped polarity, was tested,.

Figure 4A:
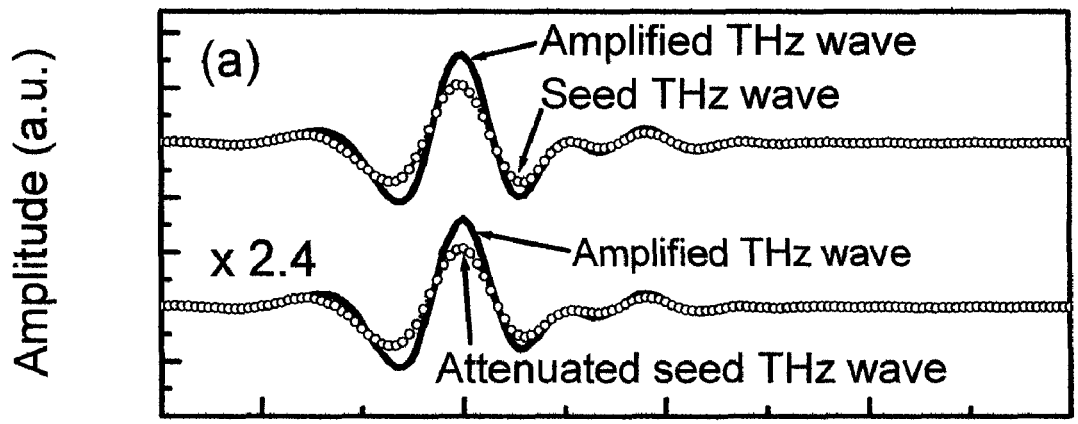
FIGS. 4A and 4B are plots of terahertz waveforms illustrating the amplification effect using the experimental setup of FIG. 1 by reducing the input terahertz signal (i.e., unamplified seed THz wave) and by flipping the input terahertz waveform (i.e., unamplified seed THz waveform), respectively, and with plots of an unamplified seed terahertz waveforms (circles) obtained by blocking the optical gain beam illustrated for comparison.
Figure 4B:
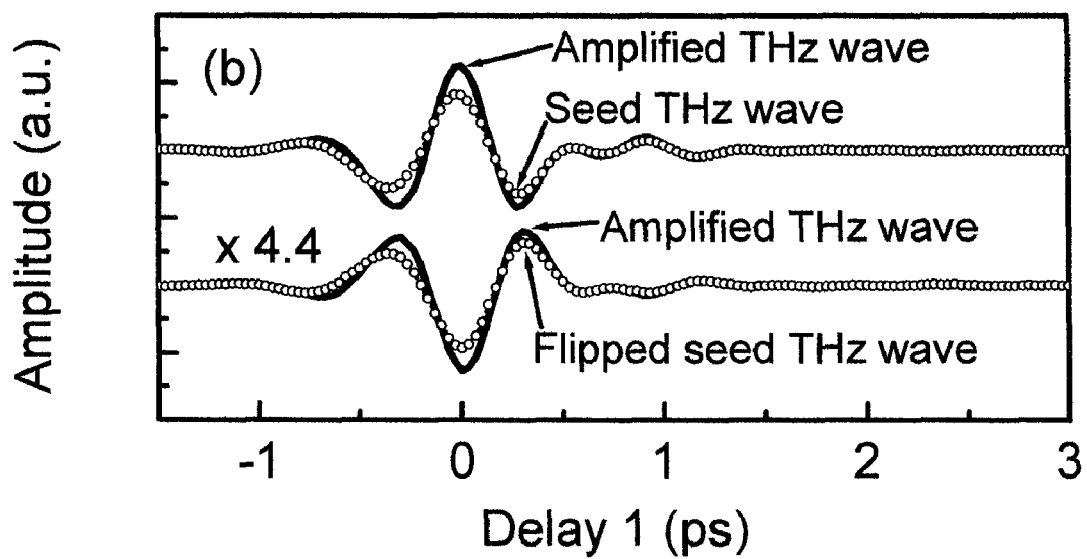

It was observed that the output terahertz signals have nearly the same enhancement percentages over the seed signals as shown in FIG. 4A with different seed terahertz strength, and as shown in FIG. 4B with the opposite seed terahertz polarity. The waveforms were obtained by scanning Delay 1 while the optical gain Delay 2 and optical probe Delay 3 were fixed at the maximum amplification percentage timing, i.e., the entire seed terahertz waveform was virtually amplified point-by-point at maximum amplification percentage when the optical pump Delay 1 was scanned. By reducing the terahertz signal by a factor of about 2.4, the amplification percentage is almost kept the same as shown in FIG. 4A. By flipping the input terahertz waveform (changing the polarity) the amplification percentage is almost kept the same, as shown in FIG. 4B. The baselines are shifted and the waveforms are enlarged for clarity.

This observation is in contrast to the inversionless amplification obtained in a solid system by C. Janke et al. "Inversionless Amplification Of Coherent Terahertz Radiation", Phys. Rev. B 67, 155206 (2003). It does not support that the interference between the optical seed beam and the optical gain beam generated terahertz waves is the dominant factor. As measured, the enhancement cannot be achieved by the constructive or destructive interference of the optical gain beam induced terahertz wave with the seed terahertz signals at different strengths or opposite polarities.

Experimental results shown in FIGS. 4A and 4B indicate that the enhancement observed is a true amplification. In the second experiment, the polarization of the optical gain beam (both the fundamental and second-harmonic) were varied while the total intensity of the beams remain nearly unchanged. In the experiment, it was observed that the terahertz wave enhancement is extremely sensitive to the polarization of the optical gain beam, i.e., the same result as the situation with only 800 nm in the optical gain beam (without BBO). This observation excludes the possibility of enhancement by the spatial profile modification of the seed terahertz wave by the conductive plasma, since the plasma density is unchanged.

As the optical gain beam intensity reaches over $4 \times 10^{14}$ W/cm$^2$, the ionization process in the ambient gas is dominated by strong-field ionization (tunnel ionization), and an ionization rate of over $10^{15}$ s$^{-1}$ is reached, which corresponds to a probability of 100% for a molecule to be ionized during a time scale of 1 fs. So the greatest possibility is the nonlinear optical parametric processes, similar to the nonlinear processes for the terahertz generation in air plasma, and it is proposed that the amplification effect may be attributed to the parametric processes during the plasma formation based on the following analysis.

From the pump-probe decay shown in FIG. 2, it is observed that after the optical gain pulses (800 nm and its second-harmonic) arrive, there is a very complicated change in the peak input terahertz signal. Only within a small time window of about 400 fs can the input terahertz signal be amplified with a net gain. The origin of optical parametric processes is the nonlinear response of the bound electron to the applied light field. Free electrons cannot have such nonlinear responses. After the high-intensity light field is applied to the air molecules but before the complete formation of the plasma, the electrons involved may be considered bound electrons and they may have a strong nonlinear response to the light field.

In our previous work, "Coherent Control of THz Wave Generation in Ambient Air", Phys. Rev. Lett. 96, 075005 (2006), it has been proven that the polarity of the terahertz waveform generated through four-wave mixing processes in air plasma may be controlled or flipped over by inducing an additional phase shift between the fundamental and its second harmonic. In the present experimental results, the negative peak, shown in FIG. 2B, may be attributed to the additional phase shift between the fundamental and its second harmonic in the optical gain beam (or terahertz electric field flipped over by the additional phase shift by the plasma formation) during the plasma formation when the plasma density is increasing dramatically.

It is noted that there is a competing effect between the amplification and the screening of the plasma. The amplification only occurred within a few hundred femtoseconds while the screening starts as soon as the plasma is formed and lasts as long as the plasma exists, as shown in FIG. 2.

The proposed nonlinear optical parametric interaction is between ($\omega$, $2\omega$, and $\Omega_{THz}$ (terahertz wave)). In the case that there is only the fundamental wavelength (800 nm) in the optical gain beam, the $2\omega$ source is the 400 nm component of the white light generated in the plasma. Because this 400 nm component is very weak compared to the 400 nm beam generated with a doubling crystal (BBO), the observed terahertz amplification effect is very weak (only 5%, see FIG. 2A). With a BBO crystal in the optical gain beam, the $2\omega$ beam is much stronger and an amplification factor of more than one order of magnitude (about 65%, as shown in FIG. 2B, higher than that in the first case was obtained). However, with a BBO crystal in the optical gain beam, the 400 nm beam intensity is several orders higher than the 400 nm component from the white light air plasma, and an even higher amplification factor is expected.

This discrepancy may be explained with the phase-matching conditions and polarizations of the $\omega$ and $2\omega$ beam in both cases. In the first case, where $2\omega$ beam is from the white-light plasma, it is automatically in phase with the $\omega$ beam, and the polarization of $2\omega$ beam is basically the same as the $\omega$ beam. With a BBO crystal (type I) in the optical gain beam, when the $2\omega$ beam is maximized, its polarization is perpendicular to that of the $\omega$ beam. So the BBO crystal needs to be rotated so that the generated $2\omega$ beam has a component in the direction of polarization of the $\omega$ beam, which not only decreases the $2\omega$ beam intensity but also makes the phase matching worse, and finally decreases the expected amplification factor.

Figure 5:
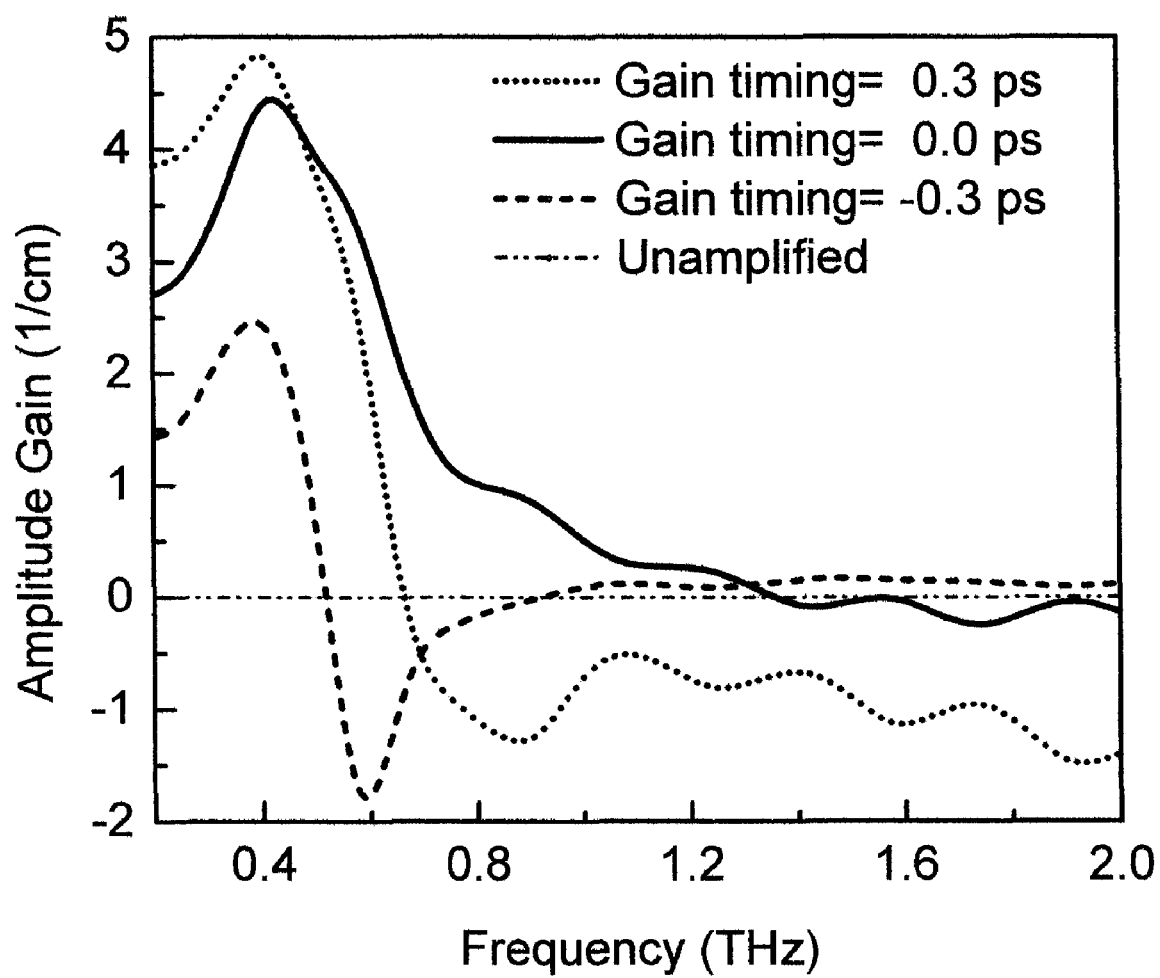
FIG. 5. illustrates plots of the terahertz field amplitude gain spectra, using the experimental setup of FIG. 1, at three different optical gain beam delay timings of 0.3 ps, 0.0 ps, and −0.3 ps, with an estimated plasma length of 5 mm and a total excitation intensity of about $8 \times 10^{14}$ W/cm$^2$, and illustrating a plot of a zero line illustrated for unamplified terahertz wave for comparison.

FIG. 5 illustrates plots of the terahertz field amplitude gain spectra at three different optical gain beam delay timings, namely, 0.3 ps, 0.0 ps, and −0.3 ps, with an estimated plasma length of 5 mm. When the optical gain beam timing is zero, the spectral gain bandwidth is the broadest. A gain from 0.2 THz to 1.2 THz is achieved with a peak gain of about 4.5/cm at 0.5 THz. In addition, when the optical gain delay is set at 0.3 ps and −0.3 ps, there is a loss in the frequency components over 0.6 THz, and over 0.5 THz, respectively.

In conclusion, experimental observation and measurements of terahertz wave amplification in fs-laser-induced plasma in gases shows that the amplification occurs only within a time scale of less than 400 fs of the onset of ionization processes. Peak electric field amplification of about 65% of the input terahertz waves in the time domain is obtained with an optical gain beam intensity of about $8 \times 10^{14}$ W/cm$^2$. Nonlinear optical parametric amplification during the plasma formation is proposed to be responsible for terahertz wave amplification in air plasma. The results provide potential to further increase the terahertz electric field in laser-induced air plasma. With a higher energy (>100 mJ) fs Ti:sapphire amplified laser system, an amplified optical pulse with longer pulse width (tens of ps) directly from the amplifier without being compressed (or being partially compressed) may be used as an optical gain pulse. Pulses compressed through a compressor may be used to generate the seed terahertz wave and to detect the amplified terahertz wave. With the above experimental scheme, it is expected that the amplification time window may be increased to the order of tens of ps so that the entire seed terahertz waveform may be amplified and higher amplification rate of the terahertz wave may be obtained.

Figure 6A:
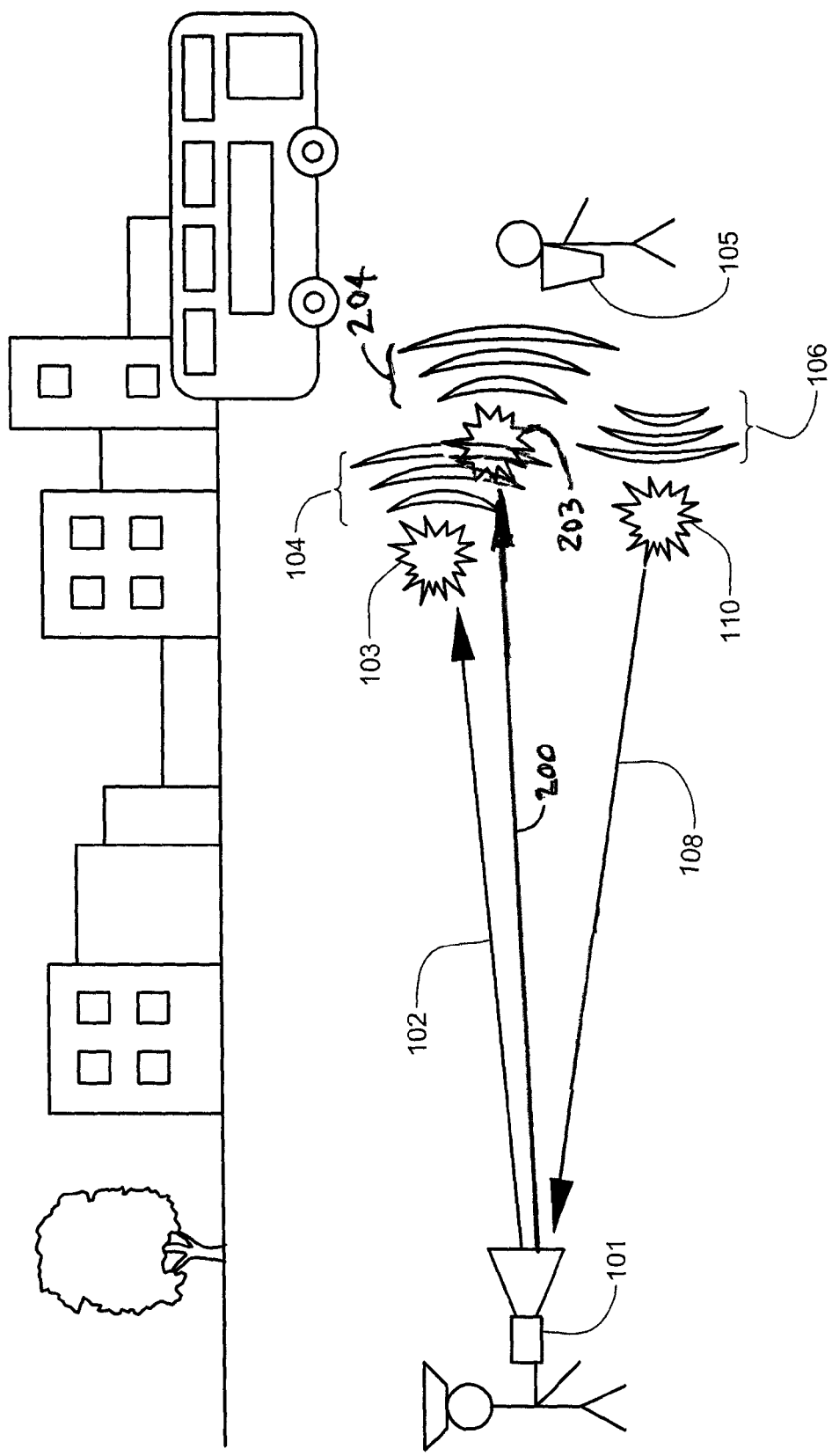
FIG. 6A illustrates one embodiment of a system for remotely analyzing an object in accordance with the present invention, wherein amplified terahertz waves reflected by an object are detected.
Figure 6B:
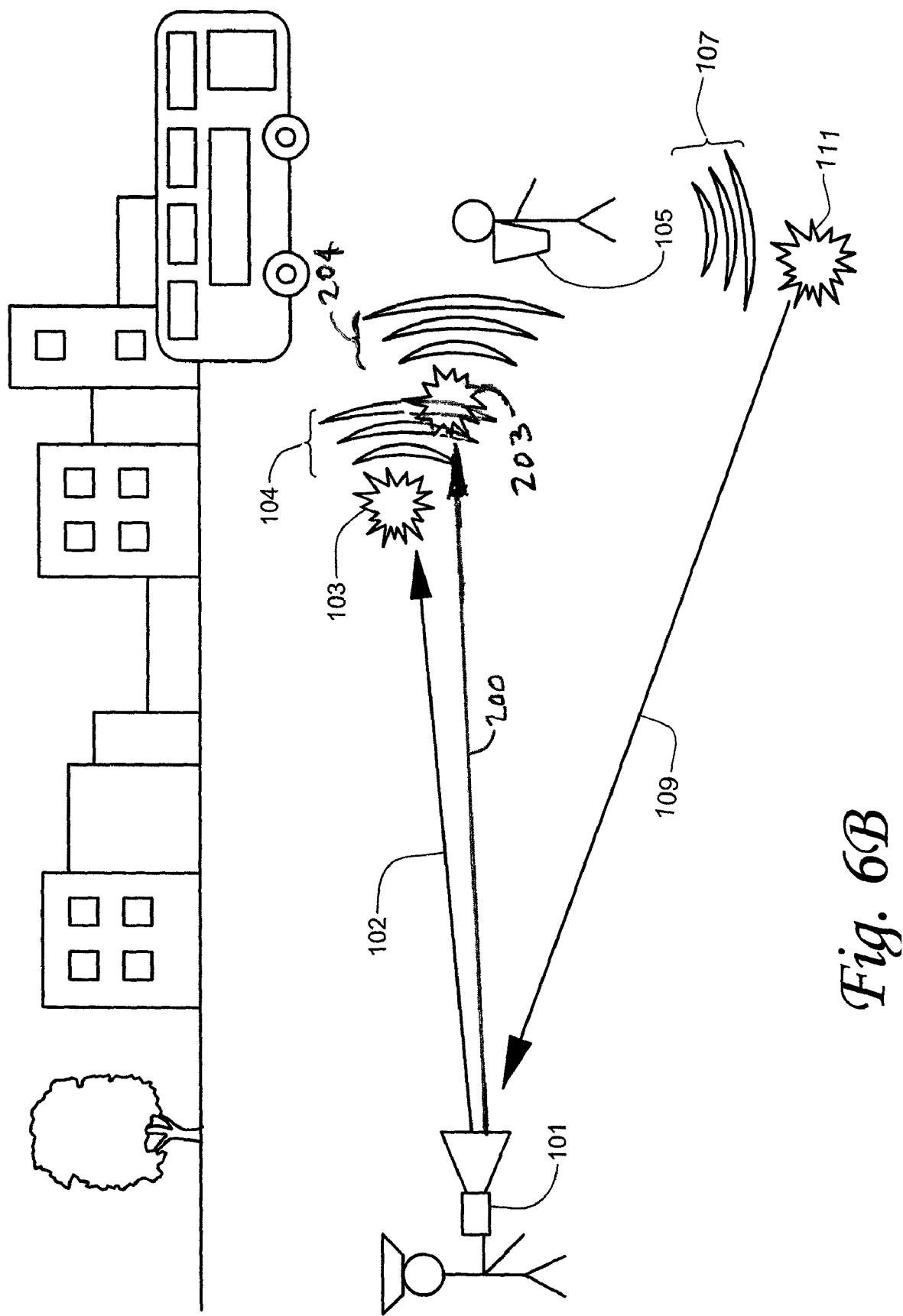
FIG. 6B illustrates one embodiment of a system for remotely analyzing an object in accordance with the present invention, wherein amplified terahertz waves scattered by an object are detected.

Turning now to FIGS. 6A and 6B, therein illustrated is one embodiment of a system 101 for remotely analyzing an object 105 in an exemplary environment in which the system may be used. In this embodiment, an operator directs a plurality of optical beams to toward a target, rather than a terahertz beam. In particular, initially an optical seed beam 102 is directed toward the target to produce a seed plasma 103 which produces a seed terahertz wave 104 directed toward the target. A second optical gain beam 200 is then directed toward the seed terahertz wave to produce an amplified terahertz wave 204 directed toward the target. The target reflects a portion of an amplified terahertz wave 204 emitted by gain plasma 203 near the object. In FIG. 6A, a terahertz wave 106 reflected by the object is sensed by sensor plasma 110 near the object. The sensor plasma 110 emits an optical wave 108, which carries the spectral signature of the object that was imposed on the reflected terahertz wave. In FIG. 6B, a terahertz wave 107 scattered by the object is sensed by sensor plasma 111 near the object. The sensor plasma 111 emits an optical wave 109, which carries the spectral signature of the object that was imposed on the scattered terahertz wave. The optical radiation emitted by the sensor plasma is detected by the remote analysis system which may be remotely located over 30 meters away from a laser source to sense the terahertz wave reflected or scattered by the object.

Figure 7A:
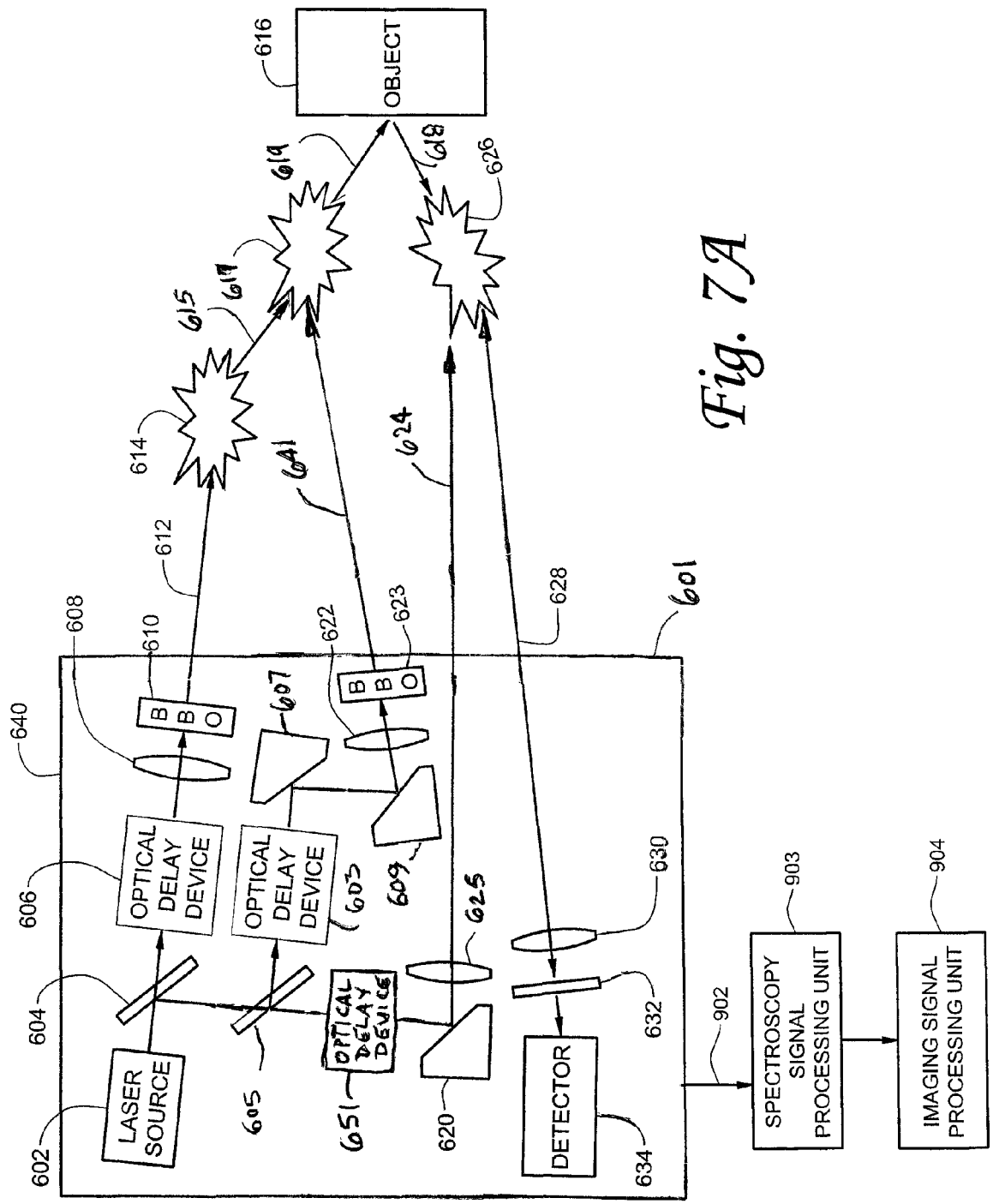
FIGS. 7A and 7B illustrate an embodiment of a system for analyzing a remotely-located object in accordance with the present invention.
Figure 7B:
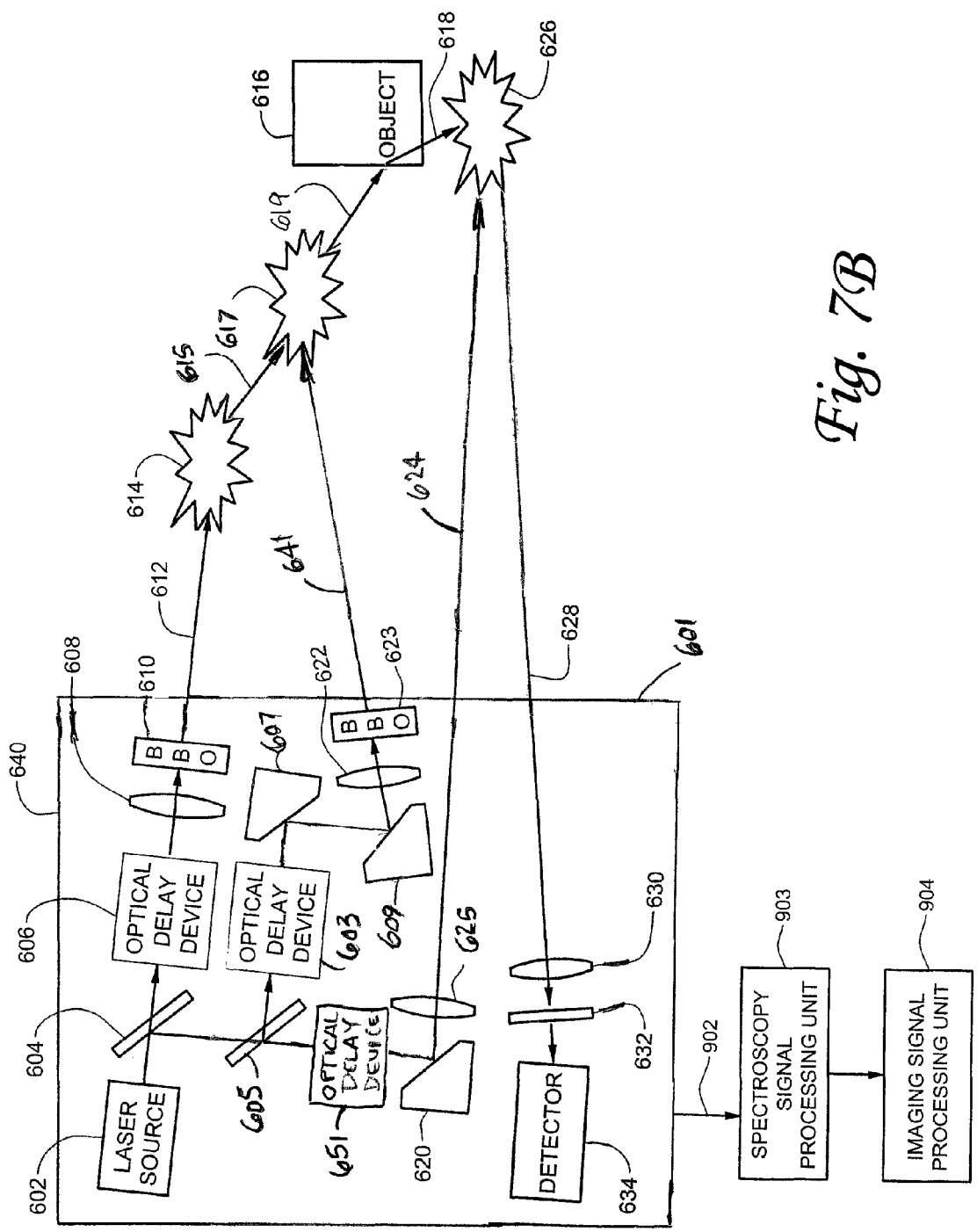

FIGS. 7A and 7B illustrate one embodiment of a system 601 for analyzing a remotely-located object, in accordance with another aspect of the present invention. This system comprises a source of an optical pump beam, means for splitting the optical pump beam into an optical seed beam and an optical gain beam, means for focusing the optical seed beam and means for focusing the optical gain beam, a source of an optical probe beam, means for focusing an optical probe beam that is modulated with a signature of a targeted object that was imposed onto detected terahertz radiation by the object, and an optical detector. The optical seed beam and the optical gain beam induce an ionized gas to generate amplified terahertz radiation that is directed toward an object to be analyzed. The amplified terahertz radiation incident to the object interacts with the object, and the object reflects (as in FIG. 7A) or scatters (as in FIG. 7B) at least a portion of the incident amplified terahertz radiation. A source of an optical probe beam provides a focused optical probe beam for ionizing a volume of ambient gas to produce a sensor plasma. The sensor plasma emits a resultant optical beam as a result of an interaction of the optical probe beam and the amplified terahertz radiation reflected or scattered by the object. The resultant optical beam emitted by the sensor plasma is detected by an optical detector such as a photomultiplier detector or a photodiode.

In the embodiment of FIGS. 7A and 7B, a source of an optical pump beam comprises laser source 602. A first beamsplitter 604 splits the optical pump beam into an optical seed beam 612 and a second optical beam. A second beam splitter 605 splits the second optical beam into an optical gain beam 641 and an optical probe beam 624. Optical seed beam 612 passes through an optical delay device 606 and a lens 608 focuses optical seed beam which comprising a fundamental frequency. One example of optical delay device 606 comprises a series of mirrors arranged to change the length of the optical radiation's propagation path of the optical seed beam. A nonlinear optical crystal 610, such as a β-barium borate (BBO) crystal, is placed between lens 608 and the focal point of the lens. The nonlinear optical crystal produces second harmonic waves. The residual fundamental waves and second harmonic waves produce a first plasma 614 and induce the emission of an intense terahertz wave 615 therefrom.

Optical gain beam 641 passes through an optical delay device 603, a fixed mirror 607, an adjustable mirror 609, and a lens 622 focuses optical gain beam which comprising a fundamental frequency. One example of optical delay device 603 comprises a series of mirrors arranged to change the length of the optical radiation's propagation path of the optical gain beam. A nonlinear optical crystal 623, such as a β-barium borate (BBO) crystal, is placed between lens 622 and the focal point of the lens. The nonlinear optical crystal produces second harmonic waves. The residual fundamental waves and second harmonic waves produce a second plasma 617 in terahertz wave 615 and induce the emission of an amplified terahertz wave 619 therefrom, as described above, propagating toward an object 616 to be analyzed.

In response to the incident amplified terahertz radiation 619, the object reflects (as in FIG. 7A) or scatters (as in FIG. 7B) a portion of the incident amplified terahertz radiation to produce reflected terahertz radiation 618 (FIG. 7A) or scattered terahertz radiation 618' (FIG. 7B).

The system of FIGS. 7A and 7B also provides optical probe beam 624, which ionizes the ambient gas in a volume to produce sensor plasma 626. Optical probe beam 624 is produced by beamsplitter 605 and passes through an optical delay device 651, adjustable mirror 620, and a lens 625. One example of optical delay device 603 comprises a series of mirrors arranged to change the length of the optical radiation's propagation path of the optical probe beam. Beamsplitter 605 directs a portion of the optical radiation to mirror 620 which directs the incident optical radiation to lens 625. Lens 625 focuses the optical radiation from mirror 620 to provide optical probe beam 624. As a result of the interaction of optical probe beam 624 and reflected or scattered amplified terahertz radiation in sensor plasma 626, a resultant optical radiation 628 is emitted from the sensor plasma.

Resultant optical radiation 628, comprising, for example, a second harmonic frequency of the optical probe beam's fundamental frequency, is collimated by lens 630 and filtered by filter 632 to attenuate background optical radiation. An optical detector 634 detects a second harmonic component of resultant optical radiation 628 that is passed by filter 632. Optical detector 634 may comprise a photomultiplier detector, for example, or a photodiode, or any suitable detector.

The detected optical component may be analyzed. For example, system 601 additionally may include imaging signal processing unit 904, which is coupled to spectroscopy signal processing unit 903 for processing signal 902 which is provided by optical detector 634 in response to the detected component of resultant optical radiation 628. Imaging signal processing unit 904 produces a spectroscopic image of the targeted object, or a feature thereof, from an output of spectroscopy signal processing unit 903. Spectroscopy signal processing unit 903 and imaging signal processing unit 904 may comprise programs of instructions that are executable on a computer, microprocessor, or digital signal processor (DSP) chip, for example.

Figure 8A:
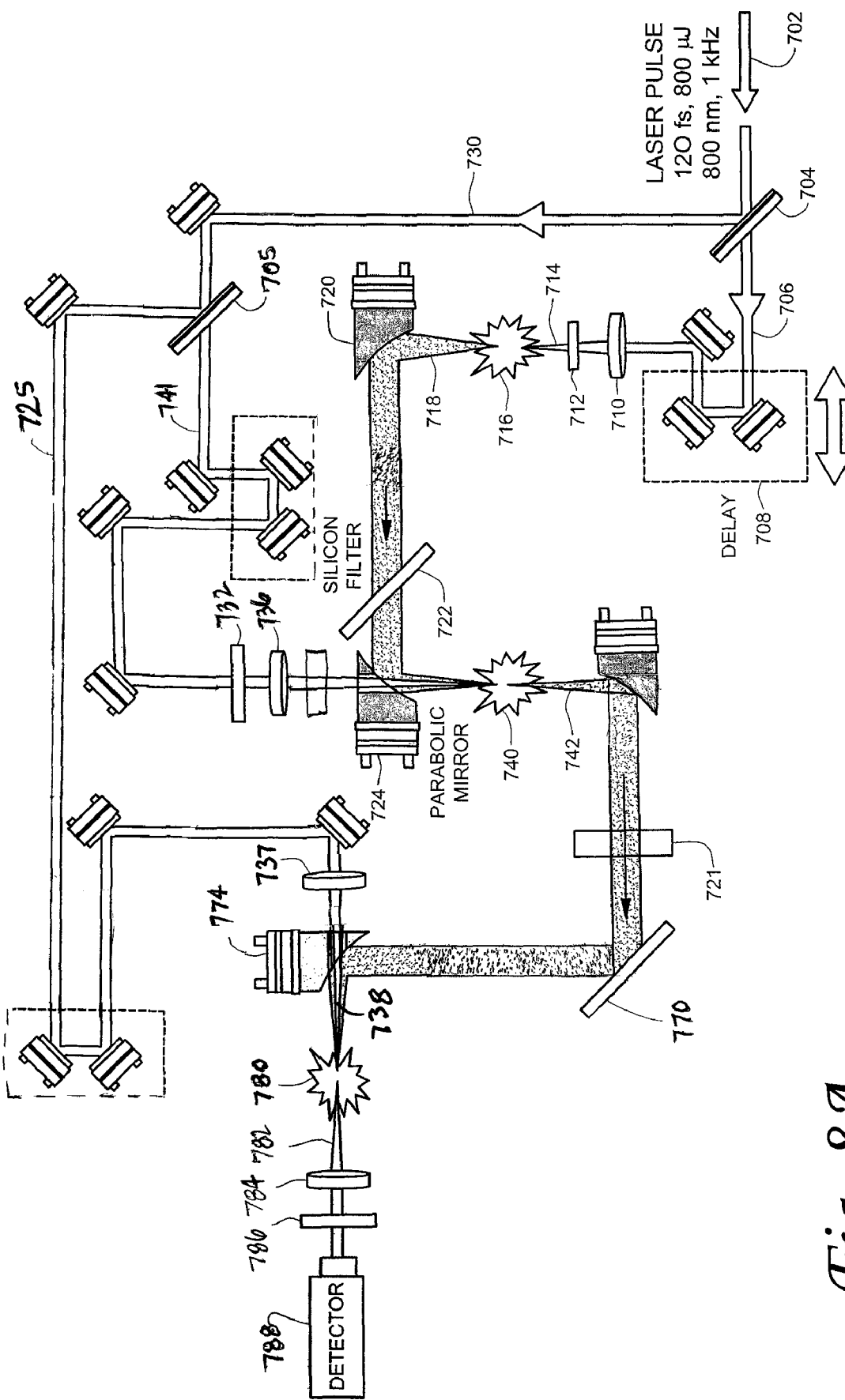
FIG. 8A illustrates an embodiment of a system that utilizes optically-induced ionized gas to emit and detect terahertz radiation to analyze objects, in accordance with the present invention, wherein a terahertz wave transmitted through a targeted object is detected.
Figure 8B:
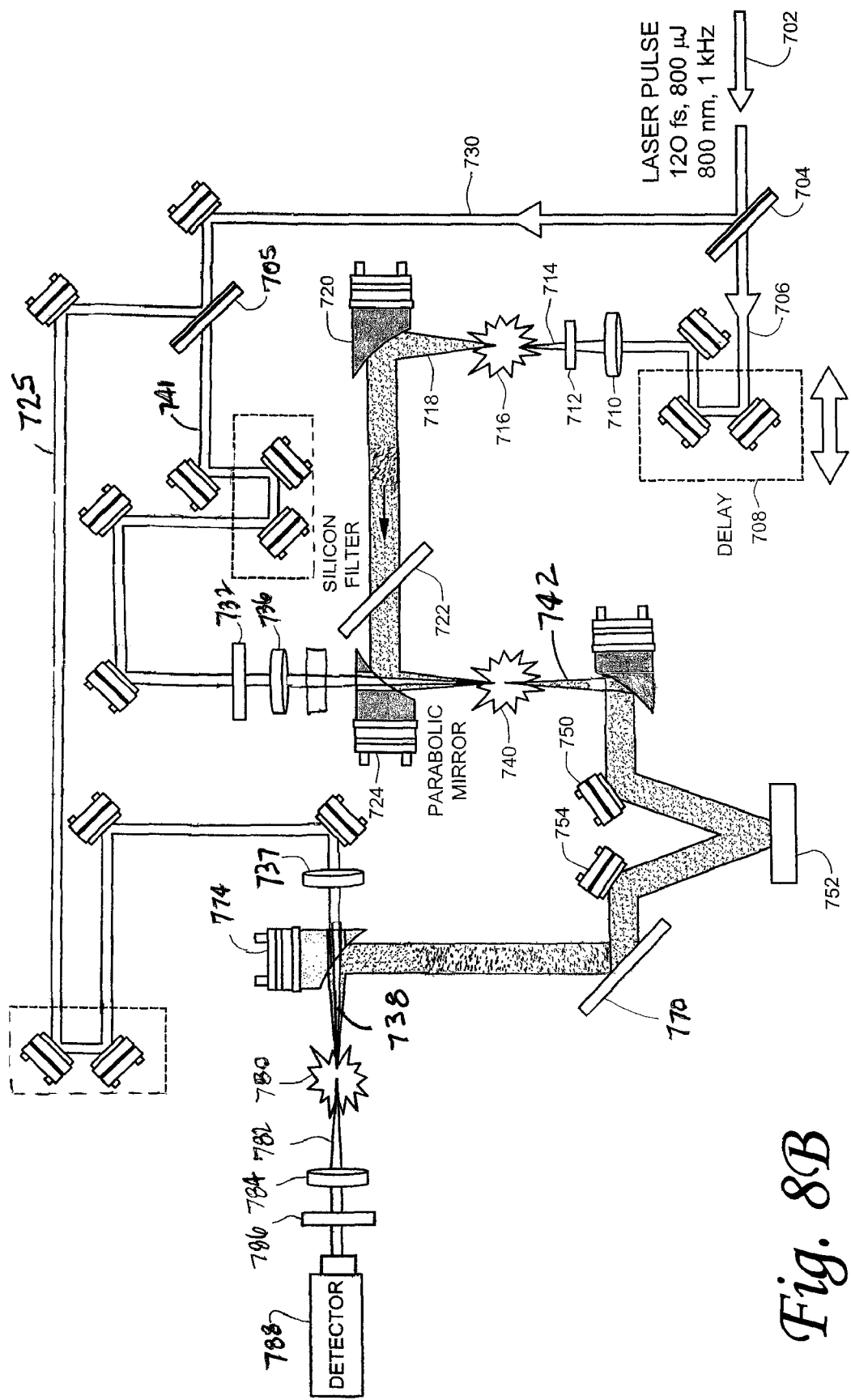
FIG. 8B illustrates an embodiment of a system that utilizes optically-induced ionized gas to emit and detect terahertz radiation to analyze objects, in accordance with the present invention, wherein a terahertz wave reflected by a targeted object is detected.

FIGS. 8A and 8B illustrate embodiments of a system that utilizes optically-induced ionized gas (plasma) to emit and detect terahertz radiation, in accordance with an aspect of the present invention. In FIG. 8A, a terahertz wave transmitted through the targeted object is measured, and, in FIG. 8B, a terahertz wave reflected by the object is measured.

A laser source such as a Ti:sapphire amplifier generates laser beam 702 comprising optical pulses. For example, the Ti: sapphire amplifier may generate 120 fs optical pulses at a repetition rate of 1 kHz with a central wavelength at 800 nm. Laser beam 702 is split into three optical beams. First, laser beam 702 is split into two beams by a beamsplitter 704. One beam, an optical seed beam 706, is used to generate initial terahertz waves. The other optical beam 730 is then split into two beams by a beamsplitter 705. One beam, an optical gain beam 741 is used to provide a gain plasma in the initial terahertz waves and generate amplified terahertz waves 742. The other beam, an optical probe beam 724, is used to detect the amplified terahertz waves passing through an object 721 in FIG. 8A or reflected from an object 752 in FIG. 8B.

Optical seed beam 706 is delayed by optical delay 708 comprising a plurality of mirrors. Delayed optical seed beam 706 is focused by lens 710. The delayed and focused fundamental pump beam is processed by a nonlinear optical device 712 to produce a composite optical pump beam 714 comprising the fundamental pump beam, having frequency ω, and its second harmonic, having frequency 2ω. In one embodiment, the nonlinear optical device comprises a 100-mm thick type-I β barium borate (BBO) crystal. The composite optical seed beam is focused in an ambient gas (for example, air) to produce emitter seed plasma 716. Composite optical seed beam 714 induces emitter seed plasma 716 to emit an intense, highly directional, broadband terahertz wave 718, which is generated through a four-wave-mixing optical process.

Terahertz wave 718 is collimated by a parabolic mirror 720. Filter 722 transmits terahertz wave 718 and blocks the residual 800 nm and 400 nm optical beams. For example, filter 722 may comprise a high-resistivity silicon wafer. Terahertz wave 718 is focused by refocusing mirror 724. In one embodiment, collimating mirror 720 has a 76.2-mm diameter with a 101.6-mm effective focal length, and refocusing mirror 724 has a 50.8-mm diameter and a 50.8-mm focal length.

A half-wavelength waveplate 732 may be utilized to control the polarization of optical gain beam 741. Lens 736 focuses the optical gain beam to produce a gain plasma 740. Both the focused optical gain beam and the focused seed terahertz wave are focused at the same point in a collinear or a quasi-collinear configuration to produce an amplified terahertz wave 742.

In FIG. 8A, amplified terahertz wave 742 is transmitted through targeted object 721, reflected off a mirror 770, and focused by refocusing mirror 774. In FIG. 8B, amplified terahertz wave 742 is directed by metal mirrors 750 and 754, and targeted object 752 reflects the terahertz wave. In both embodiments, the terahertz wave is focused by a second parabolic mirror, refocusing mirror 774, and refocusing mirror 774 has a hole to allow focused optical probe beam 725 to pass through.

A lens 737 focuses the optical probe beam in a volume of an ambient gas in which sensor plasma 780 is produced. Terahertz wave 742 is detected by the reciprocal process of its generation in which a second harmonic optical signal is produced by mixing focused probe beam 738 and the incident terahertz field. A time-resolved measurement of second harmonic optical signal 782 provides coherent detection of the amplitude and phase of terahertz field 742.

In examples of the embodiments illustrated in FIGS. 8A and 8B, the terahertz wave and the probe beam are focused at the same point a in sensor plasma 780, with estimated focal spots of about 0.8 mm and 24 μm in diameter, respectively. The terahertz-field-induced-second-harmonic optical signal is detected by a photomultiplier tube 788. Optionally, detection of second harmonic optical signal may be improved by collimating the second harmonic optical signal with a lens 784 and employing filter 786 to attenuate background optical radiation, including radiation at the optical probe beam's fundamental frequency. In the embodiments of FIGS. 8A and 8B, a unipolar waveform may be detected when the optical probe beam intensity may be less than about $1.8 \times 10^{14}$ W/cm$^2$. Above this intensity level, the detected waveform begins to change, and above approximately $5.5 \times 10^{14}$ W/cm$^2$ the measured second harmonic waveform may be bipolar and coherent detection is obtained.

The detected optical component may be analyzed and processed in a similar manner as discussed above.

Although various embodiments have been depicted and described in detail herein, it will be apparent to those skilled in the relevant art that modifications, additions, substitutions and the like can be made without departing from the spirit of the present invention and these are, therefore, considered to be within the scope of the present invention as defined in the following claims.

The invention claimed is:

1. A method for generating and amplifying terahertz radiation, the method comprising:
   inducing a first volume of a gas to produce a seed plasma and emit pulsed seed terahertz radiation by focusing an optical seed beam in the first volume; and
   amplifying the seed terahertz radiation by focusing an optical gain beam to produce a gain plasma in a second volume overlapping with the pulsed seed terahertz radiation remote from the seed plasma to increase the amplitude of the seed terahertz wave.

2. The method of claim 1 further comprising providing the optical gain beam comprising an optical radiation component having a fundamental frequency and a harmonic optical radiation component having a frequency that is harmonically related to the fundamental frequency.

3. The method of claim 1 further comprising providing the optical gain beam comprising an optical radiation component having a fundamental frequency and a second harmonic optical radiation component.

4. The method of claim 1 further comprising providing the optical gain beam comprising an optical radiation component having a fundamental frequency and a harmonic optical radiation component having a frequency that is harmonically related to the fundamental frequency, and wherein the polarization of the harmonic optical radiation component is rotated relative to the optical radiation component having the fundamental frequency.

5. The method of claim 1 further comprising optimizing the amplified terahertz radiation by providing the optical gain beam comprising an optical radiation component having a fundamental frequency and a harmonic optical radiation component having a frequency that is harmonically related to the fundamental frequency, and adjusting the polarization of the harmonic optical radiation component relative to the polarization of the optical radiation component having the fundamental frequency.

6. The method of claim 1 further comprising providing at least one pulse of optical radiation, and splitting the at least one pulse of optical radiation into the optical seed beam and the optical gain beam.

7. The method of claim 1 wherein the inducing comprises inducing the first volume of the ambient gas to produce the seed plasma near a targeted object, and the amplifying comprises amplifying seed terahertz radiation directed toward the targeted object.

8. The method of claim 1 further comprising providing at a first location at least one source for the optical seed beam and the optical gain beam, and wherein the inducing comprises inducing the volume of the ambient gas to produce the seed plasma located more than 30 meters away from the first location.

9. The method of claim 1 wherein the inducing comprises inducing the volume of the ambient gas to produce the seed plasma near a targeted object comprising at least one of an explosive material, a biological agent, and a chemical agent, and the amplifying comprises amplifying seed terahertz radiation directed toward the at least one of the explosive material, the biological agent, and the chemical agent.

10. The method of claim 1 wherein a time delay between the optical seed beam and the optical gain beam is in the order of picoseconds.

11. A system for generating and amplifying terahertz seed radiation, the system comprising:
   a source for an optical seed beam;
   means for focusing the optical seed beam to produce a focused optical seed beam that ionizes a first volume of a gas to produce a seed plasma to emit pulsed seed terahertz radiation;
   a source for an optical gain beam; and
   means for focusing the optical gain beam to produce a focused optical gain beam in a second volume to produce a gain plasma to increase the amplitude of the pulsed seed terahertz radiation, the second volume overlapping with the pulsed seed terahertz radiation remote from the seed plasma.

12. The system of claim 11 further comprising means for providing the optical gain beam comprising an optical radiation component having a fundamental frequency and a harmonic optical radiation component having a frequency that is harmonically related to the fundamental frequency.

13. The system of claim 11 further comprising means for providing the optical gain beam comprising an optical radiation component having a fundamental frequency and a second harmonic optical radiation component.

14. The system of claim 11 further comprising means for providing the optical gain beam comprising an optical radiation component having a fundamental frequency and a second harmonic optical radiation component, and wherein the polarization of the harmonic optical radiation component is rotated relative to the optical radiation component having the fundamental frequency.

15. The system of claim 11 further comprising means for optimizing the amplified terahertz radiation comprising means for providing the optical gain beam comprising an optical radiation component having a fundamental frequency and a second harmonic optical radiation component, and means for adjusting the polarization of the harmonic optical radiation component relative to the polarization of the optical radiation component having the fundamental frequency.

16. The system of claim 11 further comprising a source for providing an optical pump beam, and means for splitting the optical pump beam to provide the optical seed beam and the optical gain beam.

17. The system of claim 11 wherein said means for focusing the optical seed beam comprises means for focusing the optical seed beam to produce the focused optical seed beam to produce the seed plasma in the volume of the gas near a targeted object, and said means for focusing the optical gain beam comprises means for focusing the optical gain beam to amplify seed terahertz radiation directed toward the targeted object.

18. The system of claim 11 wherein said first source and said second source are located at a first location, and said means for focusing the optical seed beam comprises means for focusing the optical seed beam to produce the seed plasma in the volume of the gas at a second location more than 30 meters away from the first location.

19. The system of claim 11 wherein a time delay between the optical seed beam and the optical gain beam is in the order of picoseconds.

20. A method for detecting a remotely-located object, the method comprising:
inducing a first volume of a gas to produce a seed plasma to emit pulsed seed terahertz radiation directed toward a targeted object by focusing an optical seed beam in the volume;
amplifying seed terahertz radiation directed toward the target by focusing an optical gain beam to produce a gain plasma in a second volume overlapping with the pulsed seed terahertz radiation remote from the seed plasma;
ionizing a third volume of the ambient gas to produce a sensor plasma by focusing an optical probe beam in the third volume; and
detecting an optical component of resultant radiation produced from an interaction of the focused optical probe beam and an incident terahertz radiation in the sensor plasma, the incident terahertz radiation being produced by an interaction of the amplified pulsed seed terahertz radiation with the targeted object.

21. The method of claim 20 wherein the optical gain beam comprises an optical radiation component having a fundamental frequency and a harmonic optical radiation component having a frequency that is harmonically related to the fundamental frequency.

22. The method of claim 20 wherein the optical gain beam comprises an optical radiation component having a fundamental frequency and a second harmonic optical radiation component.

23. The method of claim 20 further comprising providing the optical gain beam comprising an optical radiation component having a fundamental frequency and a harmonic optical radiation component having a frequency that is harmonically related to the fundamental frequency, and wherein the polarization of the harmonic optical radiation component is rotated relative to the optical radiation component having the fundamental frequency.

24. The method of claim 20 further comprising optimizing the amplified terahertz radiation by providing the optical gain beam comprising an optical radiation component having a fundamental frequency and a harmonic optical radiation component having a frequency that is harmonically related to the fundamental frequency, and adjusting the polarization of the harmonic optical radiation component relative to the polarization of the optical radiation component having the fundamental frequency.

25. The method of claim 20 further comprising providing at least one pulse of optical radiation, and splitting the at least one pulse of optical radiation into the optical gain beam and the optical probe beam.

26. The method of claim 20 further comprising providing at least one pulse of optical radiation, and splitting the at least one pulse of optical radiation into the optical seed beam, the optical gain beam, and the optical probe beam.

27. The method of claim 20 further comprising providing at a first location at least one source for the optical seed beam and the optical gain beam, and wherein the inducing the volume comprises inducing the volume of the ambient gas to produce the seed plasma located more than 30 meters away from the first location.

28. The method of claim 20 further comprising providing at a first location at least one source for the optical probe beam, and wherein the inducing comprises inducing the third volume of the ambient gas to produce the sensor plasma located more than 30 meters away from the first location.

29. The method of claim 20 further comprising analyzing the optical component of resultant radiation to detect at least one of an explosive material, a biological agent, and a chemical agent.

30. The method of claim 20 further comprising processing the optical component of resultant radiation to produce spectroscopy analysis data, and processing the spectroscopy analysis data to detect whether the target object comprises at least one of an explosive material, a biological agent, and a chemical agent.

31. The method of claim 20 wherein a time delay between the optical seed beam and the optical gain beam is in the order of picoseconds.

32. A system for detecting a remotely-located object, the system comprising:
a source for an optical seed beam;
means for focusing the optical seed beam to produce a focused optical seed beam in a first volume of a gas to produce a seed plasma and induce an emission, from the seed plasma, of pulsed seed terahertz radiation directed toward a targeted object
a source for an optical gain beam;
means for focusing the optical gain beam to produce a focused optical gain beam in a second volume of the ambient gas overlapping with the seed terahertz radiation remote from the seed plasma to amplify seed terahertz radiation directed toward the targeted object;
a source for an optical probe beam;
means for focusing the optical probe beam to produce a focused optical probe beam that ionizes a third volume of the ambient gas to produce a sensor plasma; and an optical detector for detecting an optical component of resultant radiation produced from an interaction of a focused optical probe beam and an incident terahertz radiation in the sensor plasma, the incident terahertz radiation being produced by an interaction of amplified seed terahertz radiation with the targeted object.

33. The system of claim 32 further comprising means for providing the optical gain beam comprising an optical radiation component having a fundamental frequency and a harmonic optical radiation component having a frequency that is harmonically related to the fundamental frequency.

34. The system of claim 32 further comprising means for providing the optical gain beam comprising an optical radiation component having a fundamental frequency and a second harmonic optical radiation component.

35. The system of claim 32 further comprising means for providing the optical gain beam comprising an optical radiation component having a fundamental frequency and a second harmonic optical radiation component, and wherein the polarization of the harmonic optical radiation component is rotated relative to the optical radiation component having the fundamental frequency.

36. The system of claim 32 further comprising means for optimizing the amplified terahertz radiation comprising means for providing the optical gain beam comprising an optical radiation component having a fundamental frequency and a second harmonic optical radiation component, and means for adjusting the polarization of the harmonic optical radiation component relative to the polarization of the optical radiation component having the fundamental frequency.

37. The system of claim 32 further comprising a source for providing an optical pump beam, and means for splitting the optical pump beam to provide the optical seed beam and the optical gain beam.

38. The method of claim 32 further comprising means providing an optical pump beam, and means for splitting the optical pump beam into the optical seed beam, the optical gain beam, and the optical probe beam.

39. The system of claim 32 wherein said means for focusing the optical seed beam is operable to focus the optical seed beam to produce the focused optical seed beam that induces the volume of the ambient gas to produce the seed plasma located more than 30 meters away from said source for the optical seed beam.

40. The system of claim 32 wherein said means for focusing the optical probe beam is operable to focus the optical probe beam to produce a focused optical probe beam that induces the third volume of the ambient gas to produce the sensor plasma located more than 30 meters away from said source for an optical probe beam.

41. The system of claim 32 further comprising means for analyzing the optical component of resultant radiation to detect at least one of an explosive material, a biological agent, and a chemical agent.

42. The system of claim 32 further comprising means for processing the optical component of resultant radiation to produce spectroscopy analysis data, and processing the spectroscopy analysis data to detect whether the target object comprises at least one of an explosive material, a biological agent, and a chemical agent.

43. The system of claim 32 wherein a time delay between the optical seed beam and the optical gain beam is in the order of picoseconds.

* * * * *